(12) United States Patent
Park

(10) Patent No.: US 10,780,016 B2
(45) Date of Patent: *Sep. 22, 2020

(54) VERTICAL MOTION ADJUSTER FOR THERMOTHERAPY DEVICE

(71) Applicant: CERAGEM CO., LTD., Chungcheongnam-do (KR)

(72) Inventor: Ji Hoon Park, Chungcheongnam-do (KR)

(73) Assignee: CERAGEM CO., LTD., Chungcheongnam-do (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/506,534

(22) Filed: Jul. 9, 2019

(65) Prior Publication Data

US 2019/0328609 A1    Oct. 31, 2019

Related U.S. Application Data

(63) Continuation of application No. 13/884,209, filed as application No. PCT/KR2011/008519 on Nov. 9, 2011, now Pat. No. 10,548,806.

(30) Foreign Application Priority Data

Nov. 9, 2010   (KR) .................. 10-2010-0110787
Jun. 30, 2011  (KR) .................. 10-2011-0064845

(51) Int. Cl.
A61H 7/00     (2006.01)
A61H 15/02    (2006.01)
(Continued)

(52) U.S. Cl.
CPC ......... *A61H 7/007* (2013.01); *A61H 15/0078* (2013.01); *A61H 15/02* (2013.01);
(Continued)

(58) Field of Classification Search
CPC ...... A61H 23/004; A61H 39/04; A61H 7/007; A61H 15/0078; A61H 2201/5066;
(Continued)

(56) References Cited

U.S. PATENT DOCUMENTS 3,003,497 A   10/1961  Nunes
3,039,458 A    6/1962  Hill
(Continued)

FOREIGN PATENT DOCUMENTS

CN    2337854     9/1999
CN    1714768     1/2006
(Continued)

OTHER PUBLICATIONS

English translation for CN1714768A, espacenet.com, machine translated on Sep. 26, 2019.*
(Continued)

*Primary Examiner* — Tu A Vo
(74) *Attorney, Agent, or Firm* — Michael Best & Friedrich LLP

(57) ABSTRACT

A vertical motion adjuster for a thermotherapy device includes a conveyance unit provided with a movable member configured to move along a mat, a support unit having a first side and a second side, the first side rotatably coupled to one side of the conveyance unit, and an elevation unit installed between the conveyance unit and the support unit and configured to adjust an angle of inclination of the support unit by raising or lowering the second side of the support unit such that the second side of the support unit is moved in the shape of an arc.

26 Claims, 16 Drawing Sheets

(51) Int. Cl.
- *A61H 15/00* (2006.01)
- *A61H 39/04* (2006.01)
- *A61H 23/00* (2006.01)
- *A61H 39/06* (2006.01)
- *A61F 7/00* (2006.01)
- *A61F 7/03* (2006.01)

(52) U.S. Cl.
CPC .......... *A61H 23/004* (2013.01); *A61H 39/04* (2013.01); *A61F 7/0053* (2013.01); *A61F 7/032* (2013.01); *A61F 2007/0024* (2013.01); *A61H 39/06* (2013.01); *A61H 2015/0014* (2013.01); *A61H 2201/02* (2013.01); *A61H 2201/1215* (2013.01); *A61H 2201/1284* (2013.01); *A61H 2201/1623* (2013.01); *A61H 2201/1669* (2013.01); *A61H 2201/1676* (2013.01); *A61H 2201/1678* (2013.01); *A61H 2201/5066* (2013.01); *A61H 2201/5082* (2013.01); *A61H 2203/0456* (2013.01); *A61H 2205/04* (2013.01); *A61H 2205/081* (2013.01); *A61H 2205/083* (2013.01)

(58) Field of Classification Search
CPC ............ A61H 2201/02; A61H 2205/04; A61H 2205/083; A61H 2201/5082; A61H 2201/1284; A61H 39/06; A61H 2201/1676; A61H 2205/081; A61H 2201/1669; A61H 2201/1215; A61H 2015/0014; A61H 2201/1678; A61H 2201/1623; A61H 2203/0456; A61F 2007/0024; A61F 7/032; A61F 7/0053
See application file for complete search history.

(56) References Cited

U.S. PATENT DOCUMENTS

| | | | |
|---|---|---|---|
| 3,238,936 A | 3/1966 | Siedentop | |
| 3,405,709 A | 10/1968 | Mathers | |
| 3,812,846 A | 5/1974 | Trout | |
| 3,882,856 A | 5/1975 | Heuser et al. | |
| 4,586,493 A | 5/1986 | Goodman | |
| 5,088,475 A | 2/1992 | Steffensmeier | |
| 5,165,390 A | 11/1992 | Fleetwood | |
| 6,117,094 A | 9/2000 | Fujii | |
| 6,312,400 B1 | 11/2001 | Itikawa et al. | |
| 6,832,991 B1 | 12/2004 | Inada et al. | |
| 6,849,054 B1 | 2/2005 | Kim | |
| 7,004,916 B2 | 2/2006 | Dehli | |
| 7,052,476 B2 | 5/2006 | Kim | |
| 7,081,098 B2 | 7/2006 | Kim | |
| 7,118,541 B2 | 10/2006 | Kim | |
| 7,645,249 B2 | 1/2010 | Kim et al. | |
| 2001/0004679 A1* | 6/2001 | Ichikawa | A61H 7/001 601/98 |
| 2001/0041852 A1 | 11/2001 | Park | |
| 2002/0082534 A1 | 6/2002 | Jikiba | |
| 2002/0138023 A1 | 9/2002 | Kume et al. | |
| 2002/0193713 A1 | 12/2002 | Lee | |
| 2003/0018284 A1 | 1/2003 | Lim | |
| 2004/0260215 A1 | 12/2004 | Kim | |
| 2005/0010144 A1 | 1/2005 | Chen | |
| 2005/0015029 A1 | 1/2005 | Kim | |
| 2005/0049531 A1 | 3/2005 | Kim | |
| 2005/0090770 A1 | 4/2005 | Chen | |
| 2007/0149907 A1 | 6/2007 | Ting et al. | |
| 2008/0125683 A1 | 5/2008 | Chen | |
| 2009/0177128 A1 | 7/2009 | Fukuyama et al. | |
| 2010/0137755 A1 | 6/2010 | Nagano et al. | |
| 2012/0010049 A1 | 1/2012 | Amalaha | |

FOREIGN PATENT DOCUMENTS

| | | | |
|---|---|---|---|
| CN | 1714768 A * | 1/2006 | ............ A61H 15/02 |
| KR | 10-2001-0096093 | 11/2001 | |
| KR | 20-0268076 | 3/2002 | |
| KR | 20-0286192 | 8/2002 | |
| KR | 20-0298697 | 12/2002 | |
| KR | 20-0314459 | 5/2003 | |
| KR | 10-2004-0011260 | 2/2004 | |
| KR | 20040039150 | 5/2004 | |
| KR | 10-2004-0077139 | 9/2004 | |
| KR | 10-2006-0042367 | 5/2006 | |
| WO | 00-69388 | 11/2000 | |

OTHER PUBLICATIONS

Partial Supplementary European Search Report for Application No. 11840005.0 dated Apr. 7, 2015 (6 pages).
Supplementary European Search Report for Application No. 11840005.0 dated Oct. 8, 2015 (13 pages).
PCT/KR2011/008519 International Search Report dated Jun. 7, 2012 (3 pages).
Communication under Rule 71(3) EPC for European Application No. 11840005.0, dated Jul. 26, 2017 (5 pages).
Decision to grant a European patent pursuant to Article 97(1) EPC for European Application No. 11840005.0, dated Feb. 1, 2018 (2 pages).

* cited by examiner

VERTICAL MOTION ADJUSTER FOR THERMOTHERAPY DEVICE

CROSS-REFERENCE TO RELATED APPLICATIONS

This application is a continuation of co-pending U.S. patent application Ser. No. 13/884,209, filed May 8, 2013, which is a national stage application of International Application No. PCT/KR2011/008519, filed Nov. 9, 2011, which claims priority to Korean Patent Application No. 10-2011-0064845, filed Jun. 30, 2011, and Korean Patent Application No. 10-2010-0110787, filed Nov. 9, 2010, the entire contents of all of which are incorporated by reference herein.

FIELD

The present invention relates to a therapy device for acupressure therapy and massage, and more particularly, to a vertical motion adjuster installed at a thermotherapy device capable of simultaneously accomplishing a pressing acupressure therapy effect and a pushing acupressure therapy effect.

BACKGROUND

In recent times, a generally used thermotherapy device has been developed into a bed type thermotherapy device to maximize a therapy effect of a user's spine area for thermotherapy and far-infrared radiation.

Nowadays, most of the bed type thermotherapy devices employ a curved rail conforming to a spine area of a human body in order to provide a more accurate and precise effect on the user's spine area. However, the thermotherapy device that employs the curved rail of the related art has not been able to accomplish an acupressure therapy and massage effect with the same pressure on the neck area and the waist area corresponding to a user's therapy area. Since the curved rail of the related art is standardized and the standardized shape is always moved upward and downward in a state in which the curved rail is mounted in a mat once, in the case of users having different body sizes, a moxibustion device has not been able to accomplish the acupressure therapy and massage effect with the same pressure.

SUMMARY

In order to solve the foregoing and/or other problems, it is an aspect of the present invention to provide a vertical motion adjuster for a thermotherapy device capable of simultaneously accomplishing a pressing acupressure therapy effect and a pushing acupressure therapy effect.

The foregoing and/or other aspects of the present invention may be achieved by providing a vertical motion adjuster for a thermotherapy device including: a conveyance unit provided with a movable member configured to move along a mat; a support unit having one side coupled to the conveyance unit; and an elevation unit installed between the conveyance unit and the support unit and configured to raise or lower the other side of the support unit.

The elevation unit may include a guide member; and a rotary member in contact with the guide member.

A gear surface may be formed at one side of the guide member, and the rotary member may be a pinion meshed with the gear surface.

The gear surface may be formed inside the guide member, and the pinion may be disposed inside the guide member to come in contact with the gear surface. The plurality of guide members and the plurality of rotary members may be provided.

The plurality of guide members and the plurality of rotary members may be provided.

A driving member configured to rotate the rotary member may be installed at the conveyance unit.

A gear box configured to transmit a rotational force of the driving member to the rotary member may be installed between a rotary shaft of the rotary member and a rotary shaft of the driving member.

The conveyance unit and the support unit may be hinged through a hinge unit.

The hinge unit may include protrusion members installed at both sides of the conveyance unit; connecting members installed at both sides of the support unit; and hinge members passing through the protrusion members and the connecting members.

A support frame on which a moxibustion device is mounted is installed at an upper surface of the support unit, and the support frame is pivotally installed at a pivot shaft.

A first resilient member having one end supported by the support unit and the other end supported by the support frame may be installed at the pivot shaft, and the first resilient member may be configured to apply a resilient force to the support frame such that one moxibustion device adjacent to the coupling position of the conveyance unit and the support unit is moved upward.

A temperature detecting member configured to detect a temperature of the moxibustion device may be provided, and a second resilient member configured to apply a resilient force in a direction in which the moxibustion device is moved upward may be installed at the temperature detecting member.

The second resilient member may be a coating surrounding the temperature detecting member.

An upwardly moving distance of the one moxibustion device adjacent to the coupling position of the conveyance unit and the support unit is different from an upwardly moving distance of the other moxibustion device opposite to the one moxibustion device with respect to the pivot shaft.

The upwardly moving distance of the one moxibustion device is larger than that of the other moxibustion device.

Inclination angles may be formed at a lower end of the support frame, and the inclination angle directed toward the one moxibustion device may be set to be smaller than the inclination angle directed toward the other moxibustion device.

A protrusion may extend downward from a lower end of the support frame, inclination angles may be formed at a lower end of the protrusion, and the inclination angle directed toward the one moxibustion device may be set to be smaller than the inclination angle directed toward the other moxibustion device.

An absorption member protruding upward toward the lower end of the support frame may be formed at the upper surface of the support unit, and a height of the absorption member protruding upward toward the one moxibustion device may be larger than that of the absorption member protruding upward toward the other moxibustion device.

A gear member having a gear surface formed at one side thereof may be installed at the guide member, and the gear member may be configured as a detachable structure.

A limit switch may be installed at any one of the conveyance unit and the guide member, a detection protrusion may be installed at the other, and when the detection protrusion enters the limit switch, a lowering operation of the support unit may be stopped.

A driving member configured to rotate the rotary member may be provided, and a rotation detection member configured to detect a raising operation of the guide member may be installed at the driving member.

The coupling position of the conveyance unit and the support unit may be disposed at a position lower than an upper end surface of the support unit.

The conveyance unit and the support unit may be hinged by a hinge unit.

The hinge unit may include protrusion members installed at both sides of the conveyance unit, connecting members installed at both sides of the support unit, and hinge members passing through the protrusion member and the connecting member.

A pin hole through which a pin passes may be formed in the hinge member.

An accommodating space into which the support unit enters may be formed in the conveyance unit.

A through-hole through which the elevation unit passes may be formed in a center of the conveyance unit.

A reinforcement rib formed along an edge of the conveyance unit to surround the through-hole may be formed at a base surface of the conveyance unit.

The plurality of reinforcement ribs may be formed in a lengthwise direction of the conveyance unit.

The conveyance unit may be manufactured by a die-casting process such that the reinforcement rib, the side surface plate, and the roller fixing shaft formed at the conveyance unit are integrally formed.

A cable configured to connect a circuit member installed under the conveyance unit and a circuit member installed under the support unit may be provided, a long hole through which the cable passes may be formed in the conveyance unit, and the long hole may have a length in a lengthwise direction larger than a length in a widthwise direction.

A projection surface curved toward a center of the long hole may be formed at an inner surface in the lengthwise direction of the long hole.

A cover member may be installed at an inner surface in the lengthwise direction of the long hole.

According to the vertical motion adjuster for the thermotherapy device of the present invention, the following effects are provided.

First, since the pressing acupressure therapy effect and the pushing acupressure therapy effect can be simultaneously accomplished as the moxibustion device is moved and raised in an arc shape, the thermotherapy effect as well as the acupressure therapy effect can be improved through the moxibustion device.

Second, even in a state in which the resilient member is installed at the support unit and the support unit is raised, the acupressure therapy and massage effect can be effectively provided.

Third, the accommodating space in which the support unit is accommodated is formed in the conveyance unit to reduce the size of the apparatus, and the conveyance unit, the support unit and the gear member are configured in a detachable manner, enabling maintenance thereof.

Fourth, the through-hole through which the guide member passes is formed in the center of the conveyance unit, and the long hole through which the cable passes is formed in the conveyance unit, improving durability.

Other aspects of the invention will become apparent by consideration of the detailed description and accompanying drawings.

BRIEF DESCRIPTION OF THE DRAWINGS

The above and other aspects and advantages of the present invention will become apparent and more readily appreciated from the following description of exemplary embodiments, taken in conjunction with the accompanying drawings of which.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

DETAILED DESCRIPTION

The present invention provides a vertical motion adjuster for a thermotherapy device including: a conveyance unit provided with a movable member configured to move along a mat; a support unit having one side coupled to the conveyance unit; and an elevation unit installed between the conveyance unit and the support unit and configured to raise or lower the other side of the support unit.

An embodiment of a vertical motion adjuster for a thermotherapy device according to the present invention will be described in detail with reference to the accompanying drawings.

Figure 1:
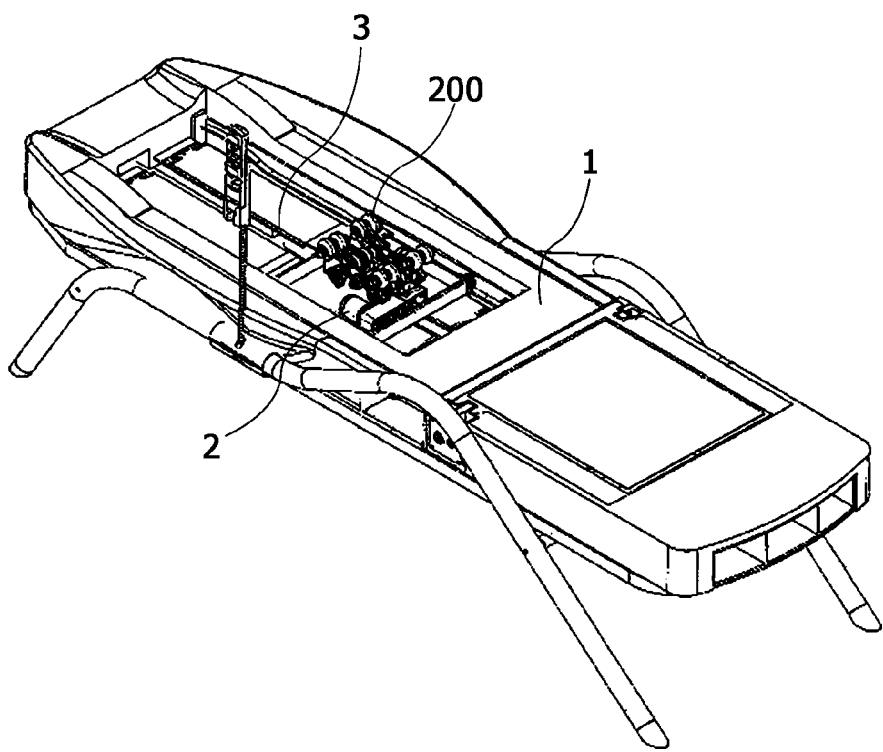
FIG. 1 is a perspective view of a thermotherapy device including a vertical motion adjuster according to the present invention.
Figure 2:
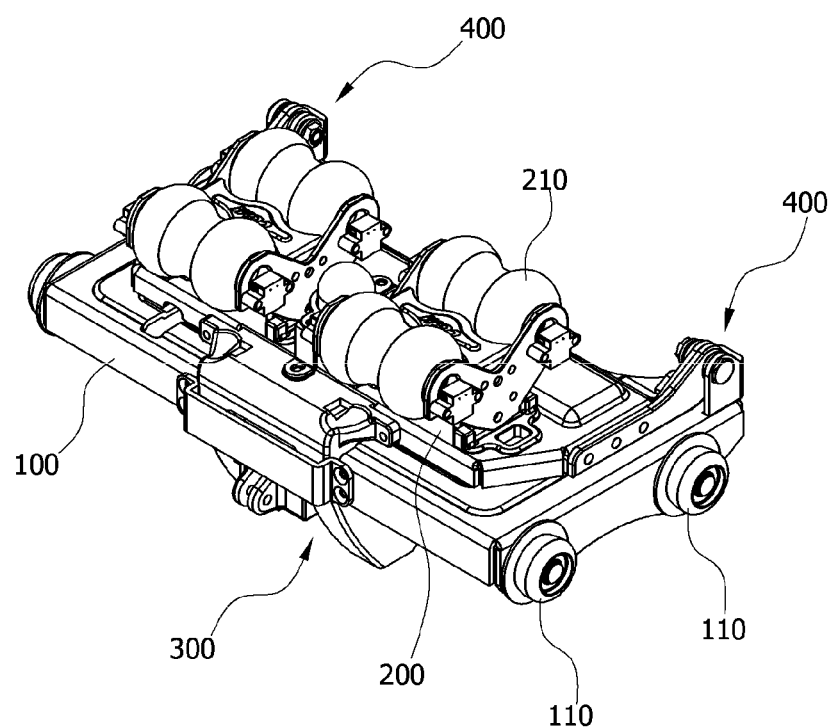
FIG. 2 is a perspective view of the vertical motion adjuster according to the first embodiment of the present invention.
Figure 3:
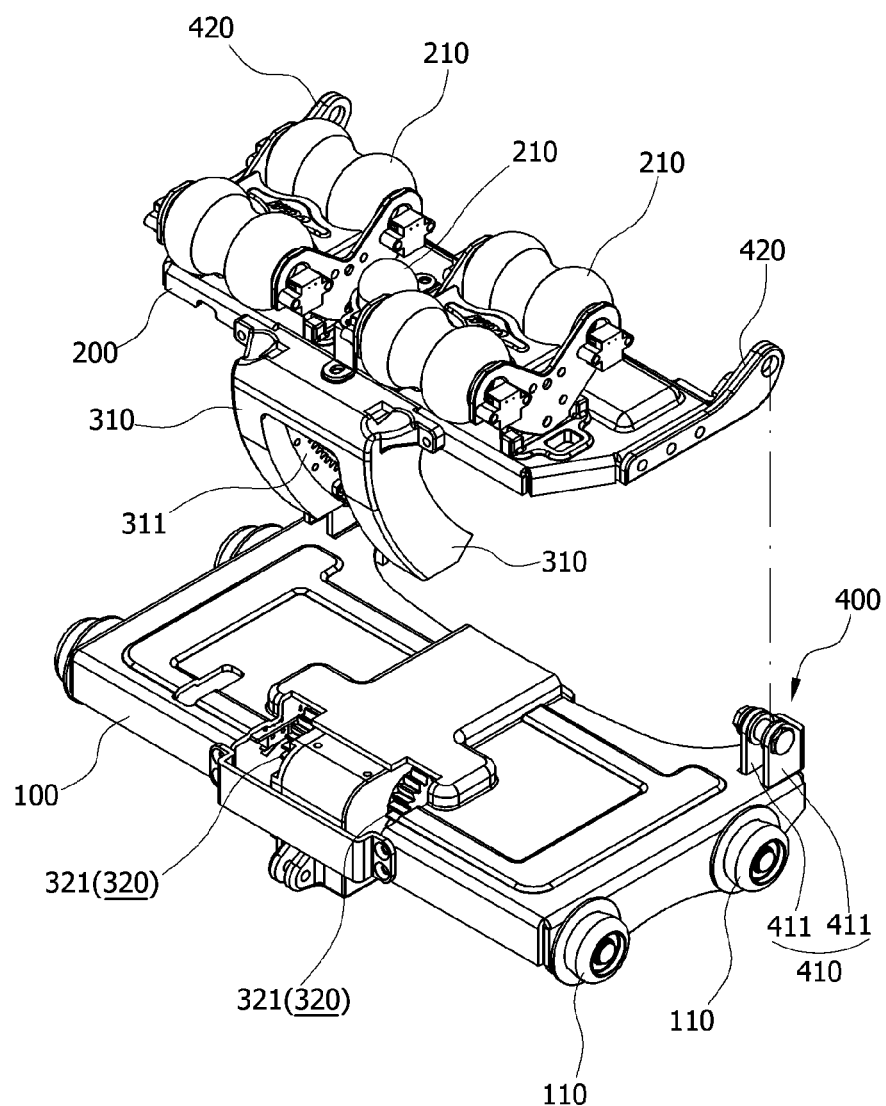
FIG. 3 is an exploded perspective view of the vertical motion adjuster according to the first embodiment of the present invention.
Figure 4:
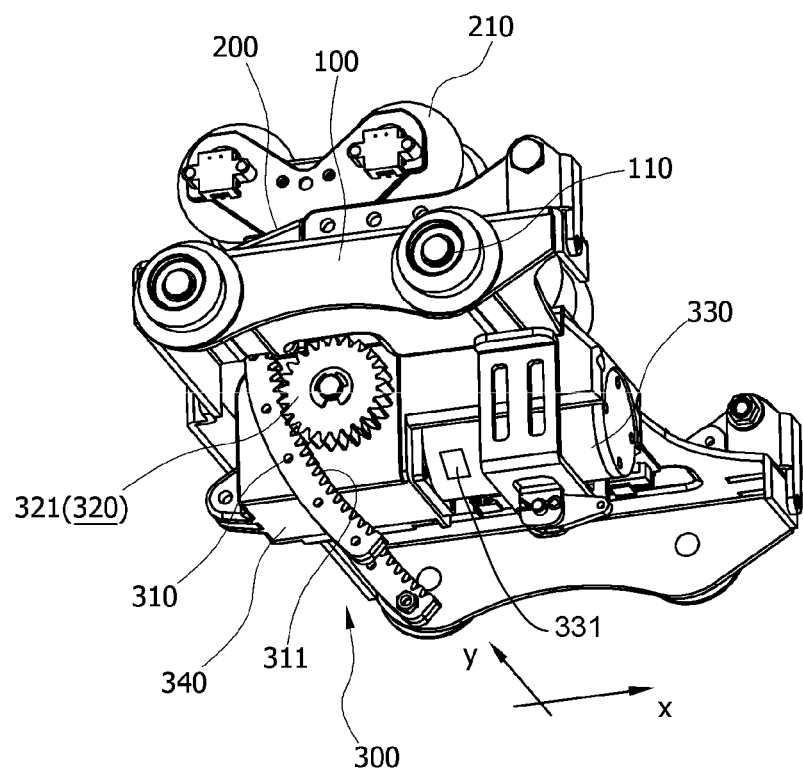
FIG. 4 is a perspective view of the vertical motion adjuster according to the first embodiment of the present invention, when seen from a lower side thereof.

FIG. 1 is a perspective view of a thermotherapy device including a vertical motion adjuster according to the present invention, FIG. 2 is a perspective view of the vertical motion adjuster according to the first embodiment of the present invention, FIG. 3 is an exploded perspective view of the vertical motion adjuster according to the first embodiment of the present invention, and FIG. 4 is a perspective view of the vertical motion adjuster according to the first embodiment of the present invention, when seen from a lower side thereof.

As shown in FIGS. 1 to 4, the thermotherapy device according to the embodiment provides the vertical motion adjuster including a conveyance unit 100 having a movable member that can move along a mat, a support unit 200 having one side coupled to the conveyance unit 100, and an elevation unit 300 disposed between the conveyance unit 100 and the support unit 200 and configured to raise or lower the other side of the support unit 200.

The thermotherapy device includes a thermotherapy mat 1 having a hollow section, and a moving apparatus configured to move the vertical motion adjuster in a major axis direction of the hollow section. According to necessity, an auxiliary mat extending from the thermotherapy mat may be further provided.

The moving apparatus includes a motor unit 2, and a conveyance unit 3 coupled to the vertical motion adjuster and configured to move the vertical motion adjuster forward and rearward in the major axis direction of the hollow section according to a rotational force of the motor unit 2. Here, the conveyance unit 3 may use various configurations such as a belt, a chain, a screw, or the like. Here, the major axis direction of the hollow section refers to a lengthwise direction of a user's spine.

While not shown, a control unit configured to control the respective devices, parts, and units, an input unit configured to receive a control input of a user, a power input unit configured to provide an external power source, and so on, may be further provided.

The conveyance unit 100 of the vertical motion adjuster includes a plate-shaped body, and movable members 110 disposed at both sides of the body. In addition, as described above, the body of the conveyance unit 100 is coupled to the conveyance unit 3 of the moving apparatus. As a result, the conveyance unit 100 can move forward and rearward in the major axis direction of the hollow section. In addition, as one end of the support unit 200 is coupled to the body of the conveyance unit 100, the support unit 200 can also move with the conveyance unit 100.

The body of the conveyance unit 100 may be constituted by a plurality of pieces, and in this case, an acupressure therapy and massage can be simultaneously performed at various areas of the user's body.

A moxibustion device 210 is placed on the support unit 200 of the embodiment. The moxibustion device 210 includes a cap type moxibustion device and a roller type moxibustion device, which are configured to provide a warm moxibustion effect and an acupressure therapy effect to the user's neck and waist areas. Accordingly, when the support unit 200 arrives at a position where the acupressure therapy is needed, the support unit 200 is raised and lowered to provide the acupressure therapy effect to the user.

One side of the support unit 200 is coupled to the conveyance unit 100, and the elevation unit 300 is provided at the other side of the support unit 200.

While the one side of the support unit 200 and the conveyance unit 100 may be hinged by a hinge member 430 (to be described later), the coupling is not limited thereto but may be performed by a bolt and a nut, and any kind of coupling is also possible as long as the other side of the support unit 200 can be raised and lowered.

The other side of the support unit 200 is raised and lowered by the elevation unit 300. As described above, since the one side of the support unit 200 is coupled to the conveyance unit 100, only the other side of the support unit 200 is raised and lowered. That is, the support unit 200 is raised and lowered while forming an inclination angle with the conveyance unit 100. Preferably, the other side of the support unit 200 is moved in an arc shape about the one side of the support unit 200.

According to the above-mentioned configuration, the moxibustion device 210 installed at the support unit 200 is moved upward and forward so that a pressing acupressure therapy effect and a pushing acupressure therapy effect can be simultaneously provided to the user.

A coupling position of the conveyance unit 100 and the support unit 200 may be the front or the rear of the support unit 200. That is, when the front of the support unit 200 is coupled thereto, the rear of the support unit 200 is moved in an arc shape, and when the rear of the support unit 200 is coupled thereto, the front of the support unit 200 is moved in an arc shape.

Here, when a moving direction of the vertical motion adjuster is set as a reference line, any one edge of edges of the support unit 200 perpendicular or crossing the reference line is fixedly coupled to the conveyance unit 100.

The elevation unit 300 is installed between the conveyance unit 100 and the support unit 200 to raise and lower the one side of the support unit 200, and thus an angle between the conveyance unit 100 and the support unit 200 is varied to raise and lower the moxibustion device 210.

The elevation unit 300 includes a guide member 310, and a rotary member 320 in contact with the guide member 310. In addition, the elevation unit 300 may further include a driving member 330 configured to rotate the rotary member 320, and a gear box 340 configured to transmit a rotational force of the driving member 330 to the rotary member 320.

The guide member 310 supports the one side of the support unit 200.

The guide member 310 has a portion in contact with the rotary member 320 and the portion in contact with the rotary member 320 may have an arc shape. According to the above-mentioned configuration, the other side of the support unit 200 can be smoothly raised and lowered.

As the rotary member 320 is rotated while the support unit 200 is lowered, the guide member 310 passes through the conveyance unit 100 and moves downward. As a result, the entire height of the vertical motion adjuster can be reduced.

The rotary member 320 is installed to come in contact with the guide member 310 to raise and lower the guide member 310.

A gear surface 311 is formed at one side of the guide member 310, and the rotary member 320 is a pinion 321 meshed with the gear surface 311.

According to the above-mentioned configuration, the gear surface 311 formed at the guide member 310 is meshed with the pinion 321 to prevent slippage of the contact area between the gear surface 311 and the pinion 321, and thus, the acupressure therapy and massage effect can be improved.

When the gear surface 311 is configured to enable attachment and detachment, maintenance thereof becomes easy.

Of course, in the embodiment, the guide member 310 is raised and lowered through a gear mechanism. However, the present invention is not limited to the gear mechanism, and various modifications may be made as long as the guide member 310 can be raised and lowered. Of course, in order to provide the above-mentioned configuration, it is effective to prevent slippage of the contact area between the guide member and the rotary member. For example, a rubber pad may be installed at areas of the guide member 310 and the rotary member 320 in contact with each other to adhere them, and a configuration of a linear motion (LM) guide type may be added to be replaced with the gear mechanism. In this case, according to necessity, the configuration of the guide member 310 may be varied.

Figure 5:
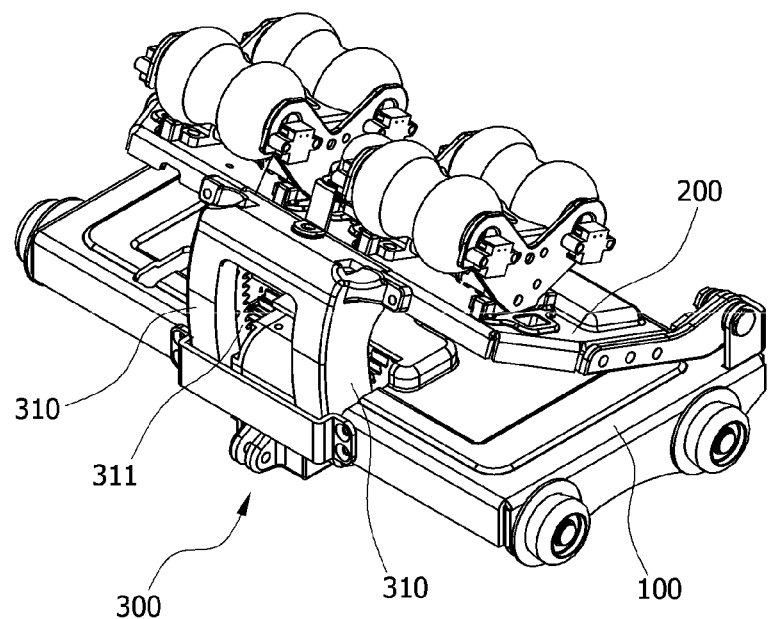
FIG. 5 is views showing a state in which a moxibustion device of the vertical motion adjuster according to the present invention is raised, FIG. 5 showing a perspective view, FIG. 6 showing an exploded perspective view, and FIG. 7 showing a perspective view when seen from a lower side thereof.

As shown in FIG. 5, the gear surface 311 is formed inside the guide member 310. The pinion 321 may be disposed inside the guide member 310 to come in contact with the gear surface 311.

Here, the inside is in a direction (a leftward direction of FIG. 4) directed toward the coupling position of the conveyance unit 100 and the support unit 200.

When the pinion 321 is rotated clockwise with respect to FIG. 4, the guide member 310 is rotated about the coupling position of the conveyance unit 100 and the support unit 200. According to the above-mentioned configuration, the guide member 310 can be rapidly raised or lowered.

As a radius of rotation is relatively reduced, a length of an arc needed to raise or lower the guide member 310 is also reduced. That is, the guide member 310 can be raised or lowered even when the pinion 321 is relatively slightly rotated, and since the pinion 321 is relatively slightly rotated, power consumption of a motor configured to rotate the pinion 321 is reduced.

The plurality of guide members 310 may be installed in a widthwise direction (a direction perpendicular to the reference line as described above) of the support unit 200. Accordingly, the support unit 200 can be prevented from being inclined toward the one side when the support unit 200 is raised and lowered.

A length in the widthwise direction of the guide member 310 may be within a certain range such that the rotary member 320 can easily raise the guide member 310.

When the length in the widthwise direction of the support unit is set to 100, a length in a widthwise direction of the guide member (a leg) may be 1 to 20.

When the length in the widthwise direction of the guide member 310 is too short, durability is weakened, the user cannot receive the acupressure therapy and massage, mass production becomes difficult due to the complicated configuration caused by the excessive length, and a space for installation of another component (for example, a motor or the like) is insufficient. In addition, the width can be variously varied according to the number of installed guide members.

In the vertical motion adjuster according to the present invention, the conveyance unit 100 includes the driving member 330 configured to rotate the rotary member 320. A BLDC motor may be used as the driving member 330.

The driving member 330 may be installed under the conveyance unit 100. Accordingly, it is effective if the rotary member 320 is also installed under the conveyance unit 100. Of course, the present invention is not limited thereto but the rotary member 320 may be installed in a space between the conveyance unit 100 and the support unit 200.

While the driving member 330 may be directly connected to the rotary member 320, when the driving member 330 cannot be directly connected to the rotary member 320 due to a structural problem, a separate configuration such as the gear box 340 may be additionally provided to connect them. In this case, maintenance of the gear box 340 and the rotary member 320 can be conveniently performed.

Due to the structural problem, as shown in FIG. 4, the driving member 330 is mounted such that the rotary shaft is disposed in a longitudinal direction (an x-axis direction, i.e., a direction of the reference line). The rotary member 320 is mounted such that the rotary shaft is disposed in a lateral direction (a y-axis direction, i.e., a direction perpendicular to the reference line). In this case, the gear box 340 is configured to transmit power from the rotary shaft in the longitudinal direction (the x-axis direction) of the driving member 330 to the rotary shaft in the lateral direction (the y-axis direction) of the rotary member 320. Of course, the present invention is not limited thereto but various members (structures, mechanisms, and so on) may be used to transmit power.

A bevel gear, a worm gear, or the like, may be used as the gear box 340 to easily transmit power when the rotary shafts are not parallel to each other.

At least one side of the conveyance unit 100 and the support unit 200 are hinged by a hinge unit 400. The hinge unit 400 includes protrusion members 410 installed at both sides of the conveyance unit 100, connecting members 420 installed at both sides of the support unit 200, and the hinge members 430 passing through the protrusion members 410 and the connecting members 420.

As shown in FIG. 3, the hinge unit 400 functions to rotatably fix one side of the support unit 200 to the conveyance unit 100.

As shown in FIG. 3, the protrusion member 410 is constituted by a pair of vertical frames 411 stood up at both sides thereof to provide a sufficient supporting force. The connecting member 420 is inserted between the vertical frames 411. The hinge member 430 passes through the pair of vertical frames 411 and the connecting member 420 and is fixed thereto to rotatably support the support unit 200.

The vertical motion adjuster according to the embodiment is a one-side opening/closing type in which the one side is raised and lowered. The moxibustion device 210 installed on the support unit 200 is configured to slightly move the user during the acupressure therapy and massage. Since a noise or impact may occur while the moxibustion device 210 is slightly moved as described above, an absorption member 230 such as a rubber material may be disposed between the support unit 200 and the moxibustion device 210.

Hereinafter, an operation of the present invention will be described below.

Figure 6:
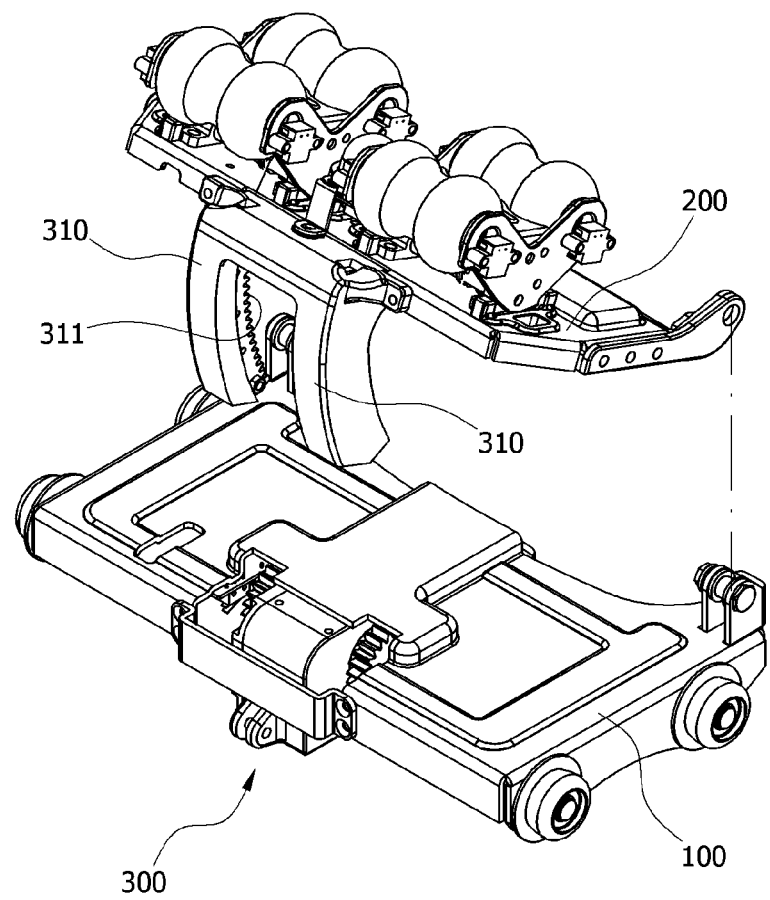
FIG. 6 is views showing a vertical motion adjuster according to a second embodiment of the vertical motion adjuster according to the present invention, FIG. 8 showing a perspective view when seen from an upper side thereof, and FIG. 9 showing a perspective view when seen from a lower side thereof.
Figure 7:
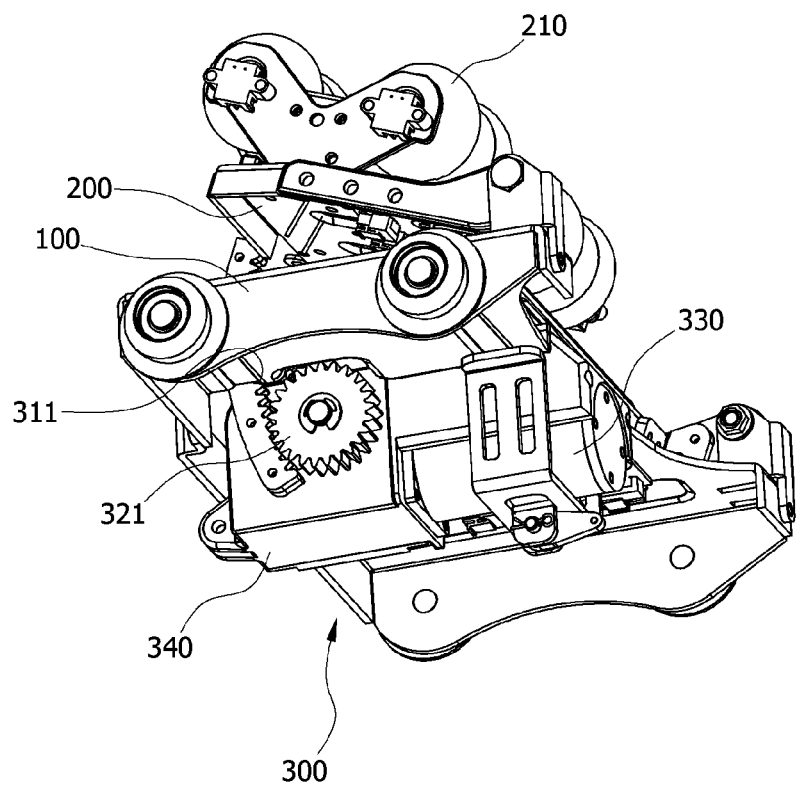

FIG. 5 is views showing a state in which the moxibustion device of the vertical motion adjuster according to the present invention is raised, FIG. 5 showing a perspective view, FIG. 6 showing an exploded perspective view, and FIG. 7 showing a perspective view when seen from a lower side thereof.

The support unit 200 basically maintains the conveyance unit 100 in a horizontal state and the moxibustion device 210 in a lowered state. As a result, as described above, the guide member 310 constituting the elevation unit 300 is configured to pass through the conveyance unit 100 to protrude downward as shown in FIG. 5.

As described above, when the driving member 330 is operated to rotate the rotary shaft of the driving member 330 in a state in which a horizontal posture of the support unit 200 is maintained, the rotary shaft of the rotary member 320 connected to the gear box 340 is rotated.

As the rotary member 320 is rotated, the guide member 310 in contact with the rotary member 320 is raised. Accordingly, as the guide member 310 installed at the other side of the support unit 200 is raised, the other side of the support unit 200 is raised about the hinge unit 400, and as shown in FIG. 5, finally, the other side of the support unit 200 is inclined upward at a certain angle.

When the rotary shaft of the driving member 330 is rotated in an opposite direction thereof, the upwardly inclined support unit 200 is lowered, and when the support unit 200 is returned to the horizontal state, rotation of the driving member 300 is stopped.

As described above, when the user receives the acupressure therapy and massage as the support unit 200 is repeatedly raised or lowered, the pressing effect and the pushing effect can be simultaneously accomplished.

Figure 8:
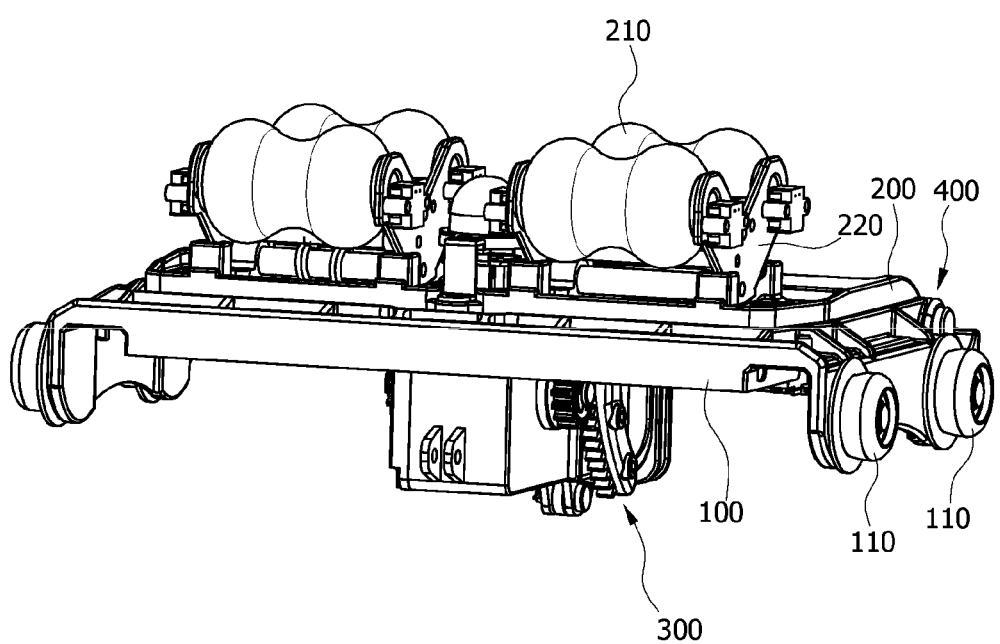
Figure 9:
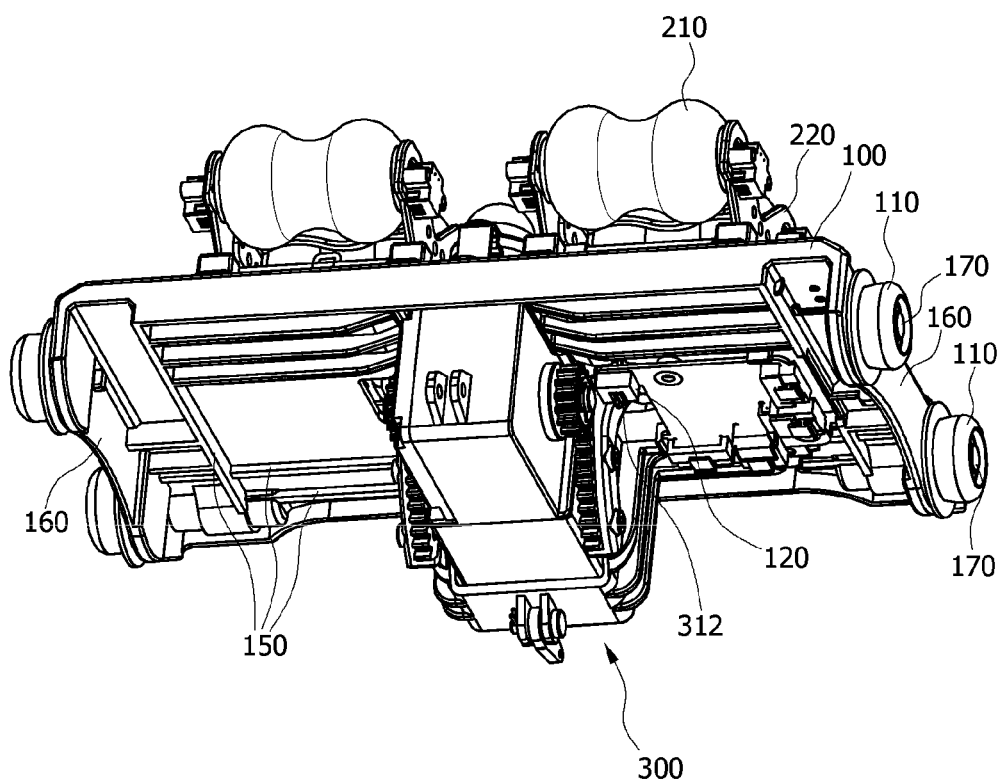
Figure 10:
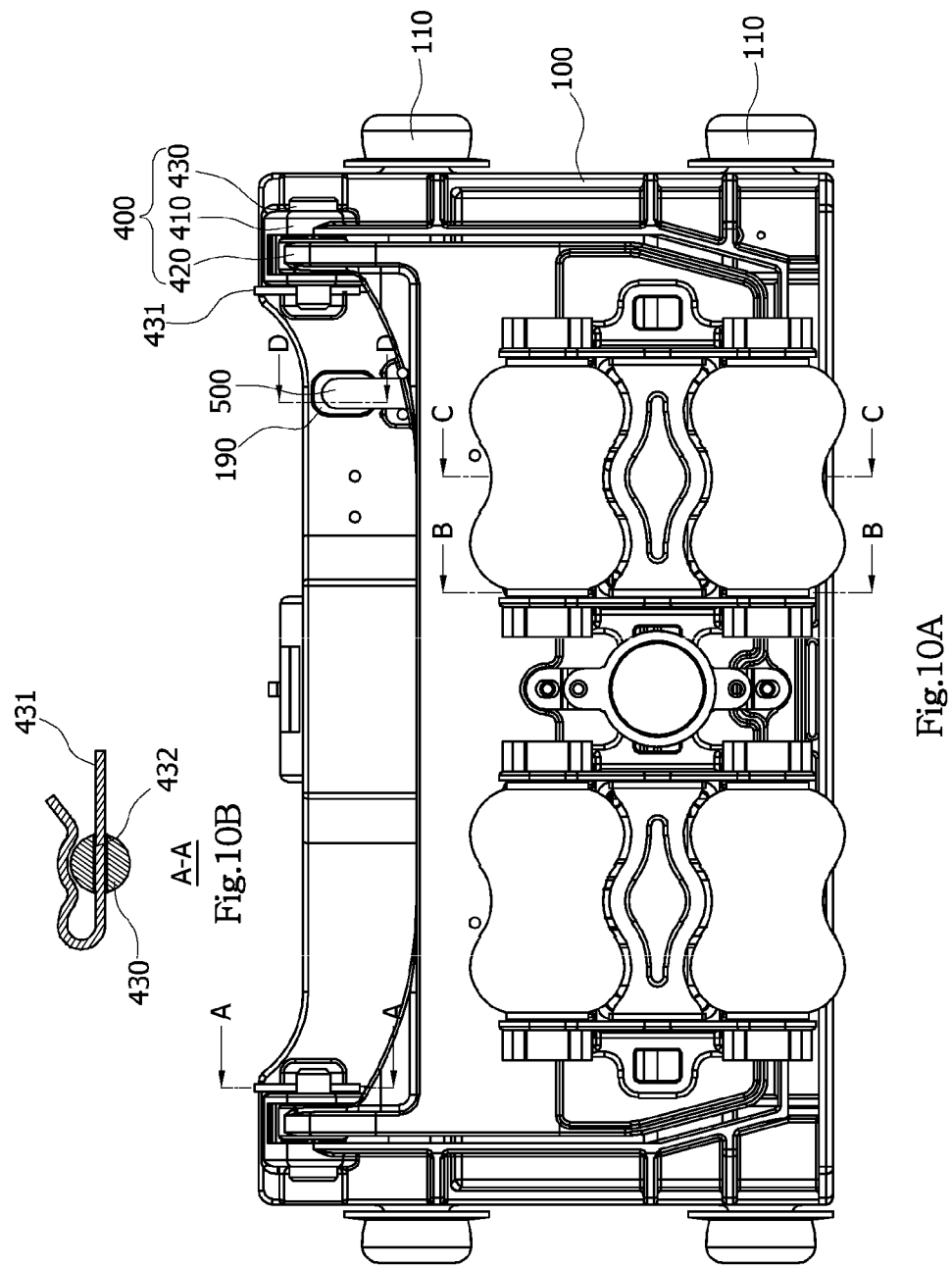
FIG. 10A is a plan view of the vertical motion adjuster according to the second embodiment of the present invention.
FIG. 10B is a cross-sectional view taken along line A-A of FIG. 10A
Figure 11:
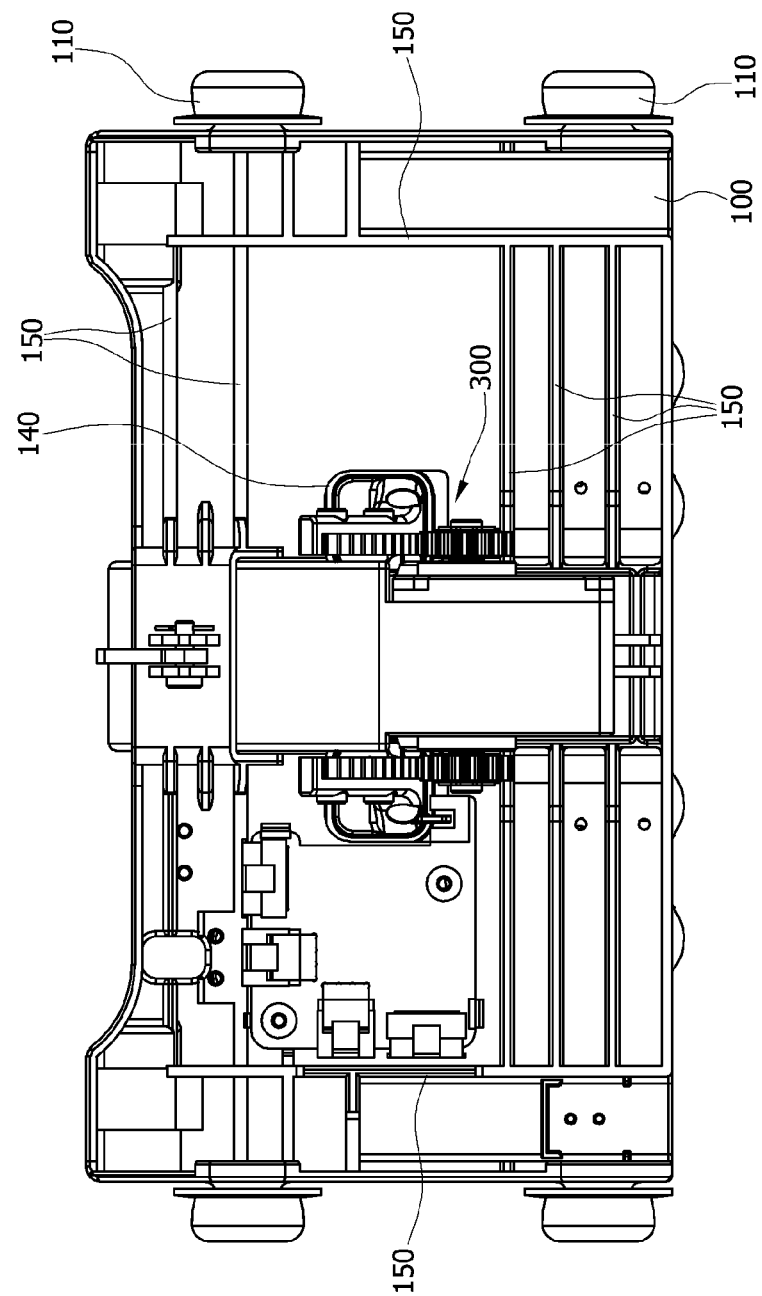
FIG. 11 is a bottom view of the vertical motion adjuster according to the second embodiment of the present invention.
Figure 12:
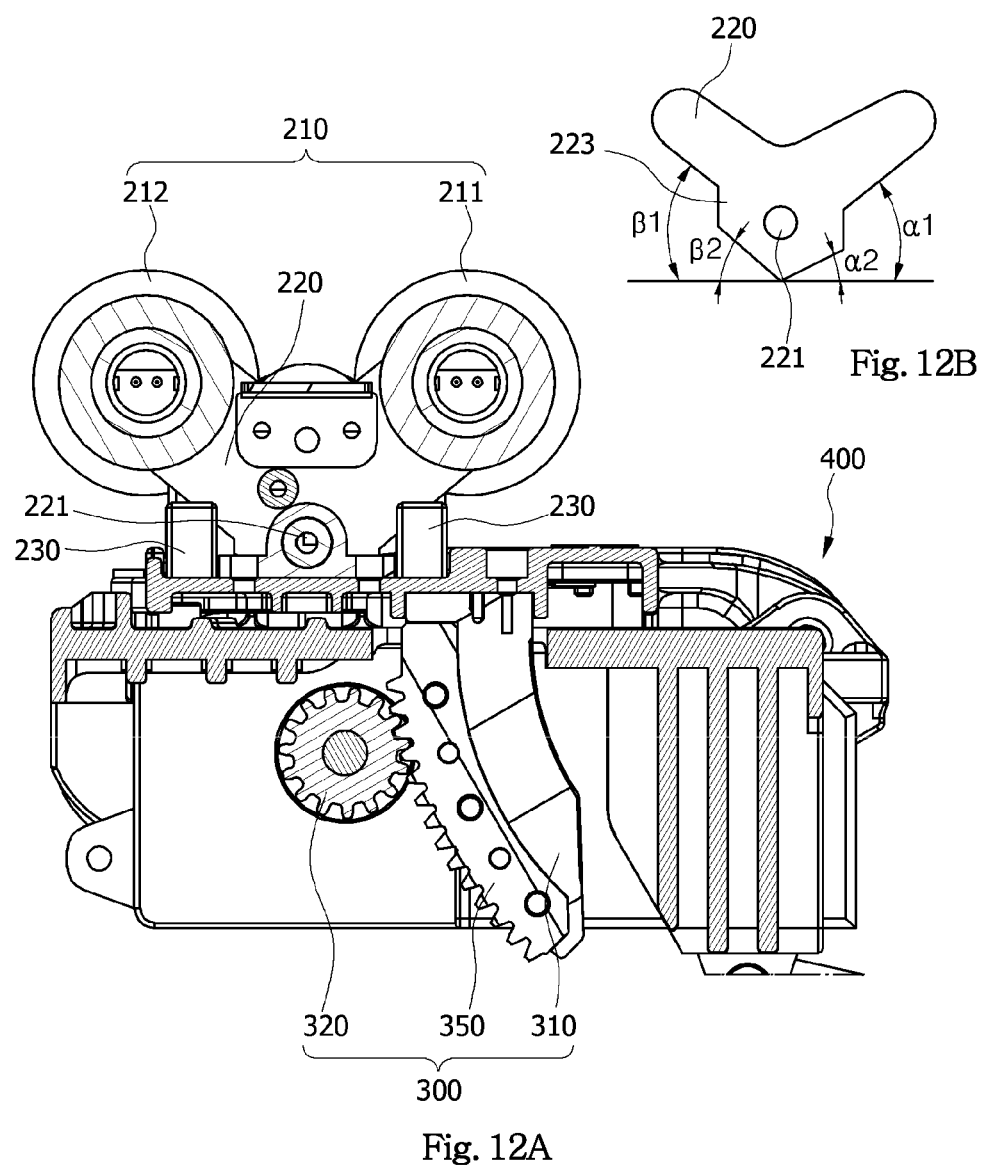
FIG. 12A is a cross-sectional view taken along line B-B of FIG. 10A
FIG. 12B is a side view of a support frame of the vertical motion adjuster of FIG. 10A.
Figure 13:
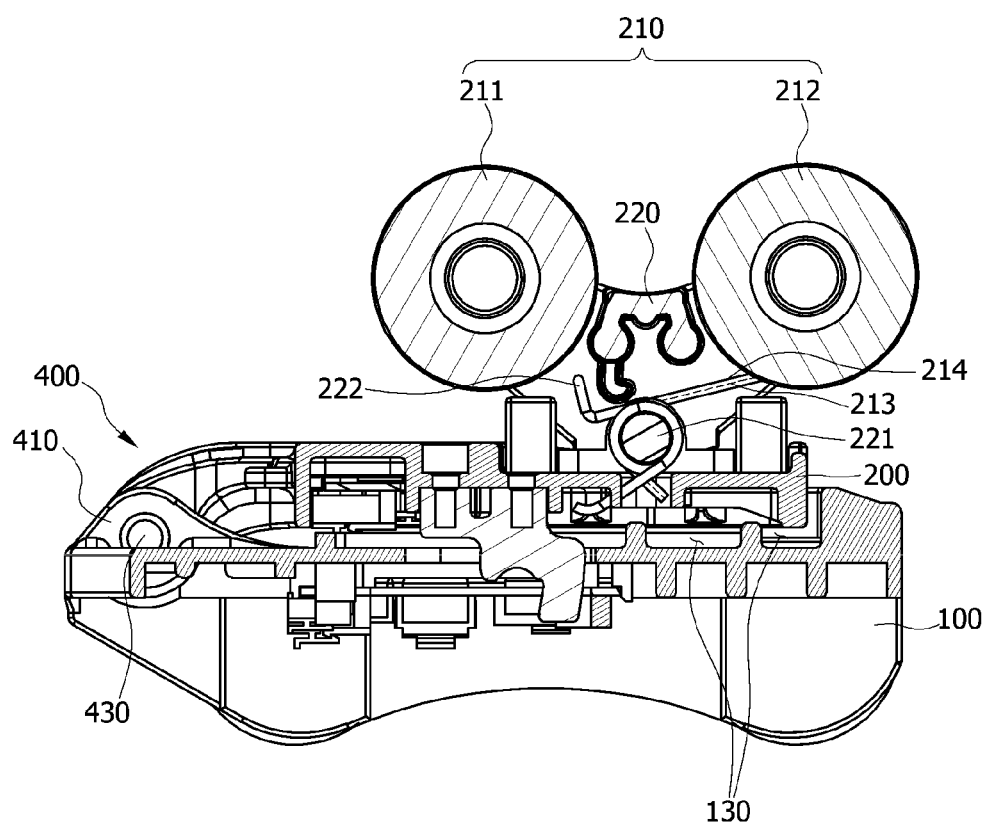
FIG. 13 is a cross-sectional view taken along line C-C of FIG. 10A.

FIG. 6 is views showing a vertical motion adjuster according to a second embodiment of the vertical motion adjuster according to the present invention, FIG. 8 showing a perspective view when seen from an upper side thereof, and FIG. 9 showing a perspective view when seen from a lower side thereof, FIG. 10A is a plan view of the vertical motion adjuster according to the second embodiment of the present invention, FIG. 11 is a bottom view of the vertical motion adjuster according to the second embodiment of the present invention, FIG. 12A is a cross-sectional view taken along line B-B of FIG. 10A, and FIG. 13 is a cross-sectional view taken along line C-C of FIG. 10A.

As shown in FIGS. 6 and 12A, the vertical motion adjuster includes a plurality of moxibustion devices 210 disposed on an upper surface of the support unit 200. The moxibustion device 210 is mounted on a support frame 220 configured to pivot about a pivot shaft 221. Accordingly, the moxibustion devices 210 can be moved upward and downward to conform to the user's body curve while the acupressure therapy and massage is performed. According to the above-mentioned configuration, even when the user's body sizes are different, the acupressure therapy and massage effect can be effectively provided.

The moxibustion devices 210 are installed at both ends of the support frame 220. Two moxibustion devices 210 are fixedly supported by one support frame 220. Of course, the present invention is not limited thereto but more than two or less than two of the moxibustion devices 210 may be fixedly supported by the one support frame 220. In addition, it is effective if the moxibustion device 210 is disposed perpendicular to an extension line of the major axis direction with respect to the reference line.

One moxibustion device 211 disposed adjacent to the coupling position of the conveyance unit 100 and the support unit 200 and the other moxibustion device 212 disposed at a position opposite to the one moxibustion device 211 with respect to the pivot shaft 221 are provided. That is, the two moxibustion devices (the one moxibustion device and the other moxibustion device) are disposed at front and rear sides with respect to the pivot shaft 221 of the support frame 220. The other moxibustion device 212 is disposed relatively closer to a coupling surface region of the conveyance unit 100 and the support unit 200 than the one moxibustion device 212.

The vertical motion adjuster according to the embodiment is configured such that the other side of the support unit 200 is raised and lowered in a state in which the one sides of the conveyance unit 100 and the support unit 200 are coupled. That is, the other side of the support unit 200 is raised in an arc shape. As the other side of the support unit 200 is raised, the horizontal state of the one moxibustion device 211 and the other moxibustion device 212 cannot be maintained, and the other moxibustion device 212 is raised to a relatively higher position than the one moxibustion device 211.

As the other moxibustion device 212 is disposed at the relatively higher position than the one moxibustion device 211, the user's weight is excessively applied to the other moxibustion device 212 only, and the acupressure therapy and massage effect is provided through the other moxibustion device 212 only.

Of course, when the user's weight is applied to the other moxibustion device 212, the support frame 220 is pivoted to move the other moxibustion device 212 downward. However, if the other moxibustion device 212 is configured to be moved downward by the user's weight only, the user may feel pain.

In the embodiment, a first resilient member 222 is provided such that the other moxibustion device 212 can be moved downward by a force smaller than the user's weight. The first resilient member 222 functions to rapidly lower the other moxibustion device 212 and simultaneously rapidly raise the one moxibustion device 211.

As shown in FIG. 13, one end of the first resilient member 222 is supported by the support unit 200, the other end is supported by the support frame 220, and the first resilient member 222 applies a resilient force to the support frame 220 such that the one moxibustion device 211 is rapidly moved upward.

That is, as the first resilient member 222 is provided, a raising operation of the one moxibustion device 211 can be rapidly performed. As a result, even in a state in which the support unit 200 is raised, since the one moxibustion device 211 and the other moxibustion device 212 can be rapidly aligned in the horizontal state, the acupressure therapy and massage effect can be effectively accomplished.

While a coil spring or a torsion spring may be used as the first resilient member 222, the present invention is not limited thereto but any elastic member such as a leaf spring may be used as long as the elastic member can apply a resilient force.

In the embodiment, a temperature detecting member 213 configured to detect a temperature of the moxibustion device 210 is provided. However, the temperature detecting member 213 should be in contact with the moxibustion device 210 even while the moxibustion device 210 is moved upward and downward. For this, in the embodiment, as shown in FIG. 13, the temperature detecting member 213 includes a second resilient member 214. The second resilient member 214 applies a resilient force in a direction in which the moxibustion device 210 is moved upward. That is, even when the moxibustion device 210 is moved upward, the temperature detecting member 213 is also moved upward by the second resilient member 214, and the contact state therebetween is not varied. When the moxibustion device 210 is moved downward, since the moxibustion device 210 is moved downward while overcoming the resilient force of the second resilient member 214, the contact state therebetween is not varied even in this case.

While a conventional coil spring or leaf spring may be used as the second resilient member 222 as described above, when a member having a resilient force is used as a coating surrounding the temperature detecting member 213, the contact state therebetween can be maintained, and the configuration can be simplified.

The one moxibustion device 211 and the other moxibustion device 212 are mounted on the support frame 220 to be moved upward and downward while the acupressure therapy and massage is performed. Here, upward and downward moving distances of the one moxibustion device 211 and the other moxibustion device 212 may be different from each other.

While there is no problem when the support unit 200 is maintained in the horizontal posture, since the other moxibustion device 212 is disposed at a position relatively higher than the one moxibustion device 211 in a state in which the support unit 200 is raised, the one moxibustion device 211 should be moved upward such that the horizontal posture of the one moxibustion device 211 and the other moxibustion device 212 is maintained.

More preferably, an upwardly movable distance of the one moxibustion device 211 may be larger than that of the other moxibustion device 212.

In order for the one moxibustion device 211 to have the upwardly movable distance larger than that of the other moxibustion device 212, as shown in FIG. 12B, inclination angles are formed at a lower end of the support frame 220. Here, an inclination angle $\alpha 1$ directed toward the one moxibustion device 211 is set to be smaller than an inclination angle $\beta 1$ directed toward the other moxibustion device 212.

In addition, a protrusion 223 extending downward is formed at the lower end of the support frame 220, and inclination angles are formed at a lower end of the protrusion 223. Here, an inclination angle $\alpha 2$ directed toward the one moxibustion device 211 may be set to be smaller than an inclination angle $\beta 2$ directed toward the other moxibustion device 212.

As shown in FIGS. 12A and 12B, the absorption member 230 protrudes upward from an upper surface of the support unit 200 toward the lower end of the support frame 220. Accordingly, an impact or the like that can be generated due to pivotal movement of the support frame 200 during the acupressure therapy and massage can be absorbed. The absorption member 230 functions to apply a resilient force to the support frame 220 as well as to absorb the impact. That is, the support frame 200 can rapidly maintain the parallel state after the pivotal movement. Here, a height of the absorption member 230 protruding upward toward the one moxibustion device 211 may be set to be larger than that of the absorption member 230 protruding upward toward the other moxibustion device 212. That is, as the height of the absorption member 230 installed under the other moxibustion device 212 is relatively lower than that of the absorption member 230 installed under the one moxibustion device 211, the upwardly movable distance of the one moxibustion device 211 is relatively increased.

A material of the absorption member 230 may be varied to adjust the resilient force applied from the absorption member 230 to the support frame 220.

While the guide member 310 according to the first embodiment is constituted by the portion extending downward to come in contact with the rotary member 320 and the portion configured to connect the upper end of the downwardly extending portion thereto, the guide member 310 according to the second embodiment is constituted by only the portion in contact with the rotary member 320.

The vertical motion adjuster according to the embodiment is manufactured through an aluminum die-casting process to improve weight reduction, productivity, and quality stability. In order to increase strength, as shown in FIG. 12A, a gear member 350 formed of steel and having a gear surface 311 formed at one side thereof is installed at the guide member 310. The gear member 350 may be configured as a detachable structure. Accordingly, the gear member 350 can be easily exchanged with a new one when the gear member 350 is worn due to repeated uses.

When the lower end of the support unit 200 comes in contact with the upper end of the conveyance unit 100 upon lowering of the support unit 200, the lowering operation should be stopped. If the rotary member 320 is rotated to lower the support unit 200 even in a state in which the lower end of the support unit 200 is in contact with the upper end of the conveyance unit 100, durability may be decreased.

In the embodiment, as shown in FIG. 9, the conveyance unit 100 includes a limit switch 120, and a detection protrusion 312 is formed at the upper end of the guide member 310 so that the lowering operation of the support unit 200 is stopped when the detection protrusion 312 enters the limit switch 120, maintaining durability. The conveyance unit 100 may include the detection protrusion 312, and the limit switch 120 may be installed at the upper end of the guide member 310.

A rotation detection member 331 (FIG. 4) may be installed at the driving member 330 configured to rotate the rotary member 320. The rotation detection member 331 is configured to detect the raising operation of the guide member 310 and stop the raising operation of the support unit 200 when the support unit 200 is raised to the highest position.

A pair of moxibustion devices 210 are arranged on the support unit 200 in a widthwise direction thereof. Accordingly, the user's body can be evenly pressed at both sides about the user's spine.

In the embodiment, as shown in FIG. 13, the coupling position of the conveyance unit 100 and the support unit 200 is formed at a position lower than an upper end surface of the support unit 200. If the coupling position of the conveyance unit 100 and the support unit 200 is formed at a position higher than the upper end surface of the support unit 200, since the coupling area comes in contact with the user while the acupressure therapy and massage is performed, the user feels irritation and inconvenience.

As shown in FIG. 10A, the conveyance unit 100 and the support unit 200 are hinged by a hinge unit 400, and the hinge unit 400 is constituted by protrusion members 410 disposed at both sides of the conveyance unit 100, connecting members 420 disposed at both sides of the support unit 200, and hinge members 430 passing through the protrusion members 410 and the connecting members 420. That is, the conveyance unit 100 and the support unit 200 are configured to be easily separated from each other to enable easy maintenance.

A horizontal position through which the hinge member 430 passes is formed at a position lower than the upper end surface of the support unit 200. That is, the horizontal position of the connecting member 420 installed at the support unit 200 and the protrusion member 410 installed at the conveyance unit 100 is formed at a position lower than the upper end surface of the support unit 200. One end of the connecting member 420 installed at the support unit 200 may extend downward to be inserted into the conveyance unit 100.

As shown in FIG. 10B, a pin hole 432 through which a pin 431 passes may be formed in the hinge member 430. The pin 431 may have an R shape. Accordingly, the hinge member 430 cannot be easily separated therefrom while the acupressure therapy and massage is performed.

As shown in FIG. 13, the conveyance unit 100 may have an accommodating space 130 that the support unit 200 can enter. The conveyance unit 100 is constituted by a bottom plate and a side surface plate 160, and the support unit 200 is inserted into the accommodating space 130 surrounded by the bottom plate and the side surface plate 160.

When the support unit 200 enters the accommodating space 130, a vertical thickness of the vertical motion adjuster according to the embodiment is reduced to form a compact configuration.

As shown in FIG. 11, a through-hole 140 through which the elevation unit 300 passes is formed in the center of the conveyance unit 100. More specifically, the guide member 310 passes through the through-hole 140. If the through-hole 140 is formed close to the edge of the conveyance unit 100, a crack may occur due to an impact applied to the conveyance unit 100. In the embodiment, the through-hole 140 is formed at the center of the conveyance unit to prevent generation of the crack.

In addition, in order to effectively prevent generation of the crack, a reinforcement rib 150 is formed at a base surface of the conveyance unit 100. The reinforcement rib 150 is formed along the edge of the conveyance unit 100 to surround the through-hole 140.

Here, the plurality of reinforcement ribs 150 may be formed in a lengthwise direction of the conveyance unit 100. The conveyance unit 100 has a length in a lengthwise direction smaller than that in a widthwise direction. This is because cracks are more frequently generated in the lengthwise direction.

In the embodiment, the guide member 310 is disposed at the center of the conveyance unit 100, and the gear member 350 is detachably installed at the outside of the guide member 310 (a leftward direction of FIG. 12A). In addition, the rotary member 320 is also installed at the outside of the guide member 310. The user's weight is transmitted to the support unit 200 when the support unit 200 is raised and lowered. If the rotary member 320 is installed inside the guide member 310, the guide member 310 may be spaced apart from the rotary member 320 due to the transmitted weight. Like in the embodiment, when the rotary member 320 is installed outside the guide member 310, a contact force between the guide member 310 and the rotary member 302 is increased by the user's weight, and the elevation can be stably performed.

When the vertical motion adjuster is not manufactured by the conventional die-casting process, a side surface of the conveyance unit 100 is bent to form the side surface plate 160, the reinforcement rib 150 is attached to the base surface of the conveyance unit 100 by welding, and a roller fixing shaft 170 is fixed to the side surface plate 160 by welding, so that work becomes complicated and a dimension tolerance is increased due to thermal deformation by the welding.

As described above, the vertical motion adjuster according to the embodiment is manufactured through an aluminum die-casting process, and as shown in FIG. 9, the reinforcement rib 150, the side surface plate 160 and the roller fixing shaft 170 are integrally formed, improving weight reduction, productivity, and quality stability.

Figure 14:
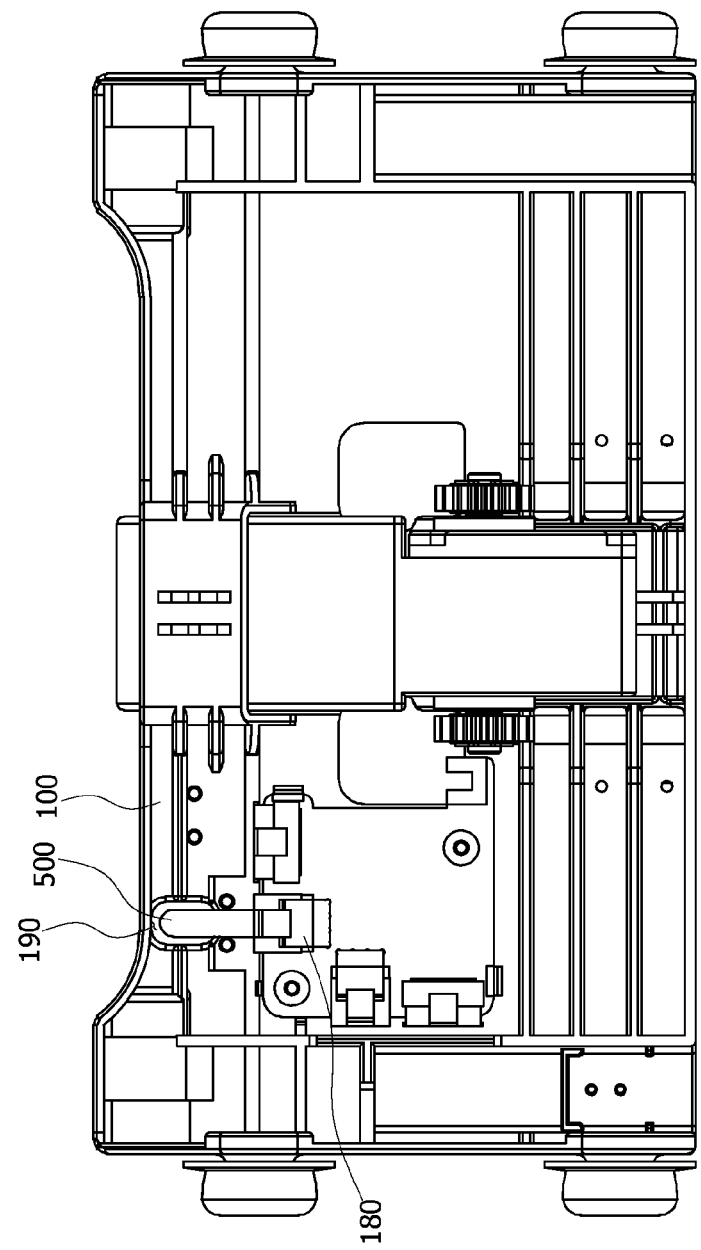
FIGS. 14 and 15 are exploded views of the vertical motion adjuster according to the second embodiment of the present invention, FIG. 14 showing a bottom view of a support unit, and FIG. 15 showing a bottom view of a conveyance unit.
Figure 15:
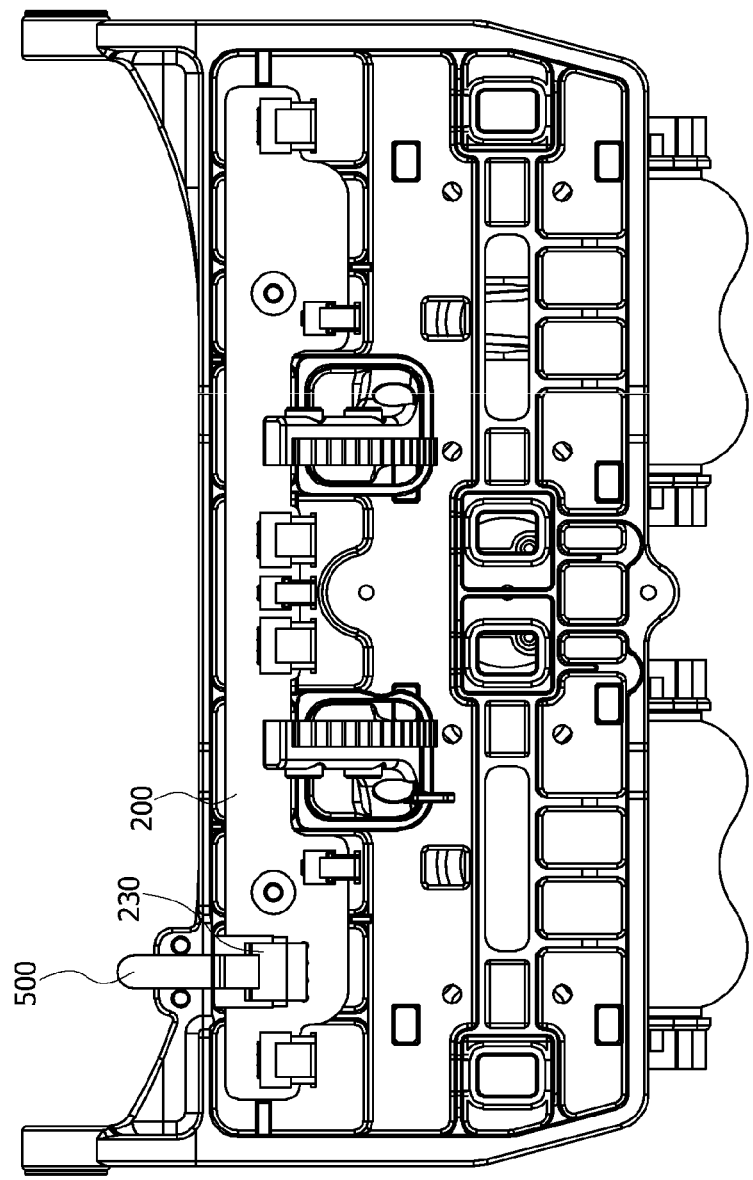
Figure 16:
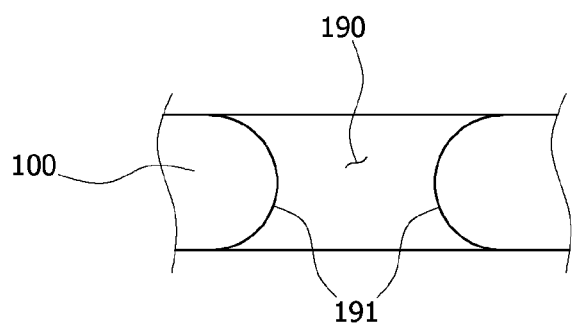
FIG. 16 is a cross-sectional view taken along line D-D of FIG. 10A.

FIGS. 14 and 15 are exploded views of the vertical motion adjuster according to the second embodiment of the present invention, FIG. 14 showing a bottom view of a support unit, FIG. 15 showing a bottom view of a conveyance unit, and FIG. 16 showing a cross-sectional view taken along line D-D of FIG. 10A.

As shown in FIG. 14, a cable 500 for signal transmission and power supply is installed between circuit members 180 and 230 installed at the conveyance unit 100 and the support unit 200, respectively. The cable 500 extends from the circuit member 180 installed under the conveyance unit 100 to the circuit member 230 installed at the support unit 200. Here, the cable 500 may pass through a long hole 190 formed in the support unit 200 rather than an outer edge of the support unit 200 to be connected thereto. If the cable 500 passes through the outer edge of the support unit 200 and is connected thereto, the cable 500 is exposed to the outside and durability may be easily decreased.

However, as shown in FIG. 15, the long hole 190 through which the cable 500 passes may have a length in the lengthwise direction larger than that in the widthwise direction. This is because when the support unit 200 is repeatedly raised or lowered, the cable 500 is moved forward and rearward in the lengthwise direction. As described above, when the long hole 190 is elongated in the lengthwise direction, since a space in which the cable 500 can move forward and rearward is formed, durability of the cable 500 can be maintained.

As shown in FIG. 16, a projection surface 191 curved toward the center of the long hole 190 may be formed in an inner surface having the long hole 190. This is because the cable 500 comes in contact with the curved projection surface 191 during repeated forward and rearward movement to maintain durability. More preferably, the projection surface 191 may be formed in only an inner surface in the lengthwise direction of the long hole 190. This because the cable 500 is mainly moved forward and rearward, and if the projection surface 191 is also formed in an inner surface in the widthwise direction, work may become complicated and productivity may be decreased.

The foregoing description concerns an exemplary embodiment of the invention, is intended to be illustrative, and should not be construed as limiting the invention. The present teachings can be readily applied to other types of devices and apparatuses. Many alternatives, modifications, and variations within the scope and spirit of the present invention will be apparent to those skilled in the art.

Various features of the invention are set forth in the following claims.

What is claimed is:

1. A vertical motion adjuster for a thermotherapy device comprising:
    a conveyance unit provided with a movable member configured to move along a mat;
    a support unit having a first side and a second side, the first side rotatably coupled to the conveyance unit; and
    an elevation unit installed between the conveyance unit and the support unit and configured to adjust an angle of inclination of the support unit between a raised position and a lowered position by raising or lowering the second side of the support unit such that the second side of the support unit is moved in the shape of an arc,
    wherein the conveyance unit includes a plate-shaped body having an upper side,
    wherein the elevation unit includes a guide member extending through an opening in the upper side,
    wherein the guide member is configured to move through the opening to adjust the angle of inclination of the support unit,
    wherein the support unit includes a support side on which a moxibustion device is mounted and a lower side opposite the support side, wherein the lower side of the support unit is spaced from the upper side of the conveyance unit when the support unit is in the raised position, and wherein the lower side of the support unit is configured to be relatively less spaced from or in contact with the upper side of the conveyance unit when the support unit is in the lowered position.

2. The vertical motion adjuster according to claim 1, wherein the elevation unit further comprises a rotary member in contact with the guide member.

3. The vertical motion adjuster according to claim 2, wherein the guide member includes a detachable gear surface installed inside the guide member, and the rotary member is a pinion installed inside the guide member and configured to mesh with the detachable gear surface.

4. The vertical motion adjuster according to claim 2, wherein the guide member is one of a plurality of guide members, and the rotary member is one of a plurality of rotary members.

5. The vertical motion adjuster according to claim 2, wherein the conveyance unit includes a driving member configured to rotate the rotary member, and wherein the elevation unit includes a gear box configured to transmit a rotational force of the driving member to the rotary member, the gear box installed between a rotary shaft of the rotary member and a rotary shaft of the driving member.

6. The vertical motion adjuster according to claim 2, further comprising a gear member having a gear surface formed at one surface thereof, wherein the gear member is installed at the guide member, and the gear member is configured as a detachable structure.

7. The vertical motion adjuster according to claim 2, further comprising a limit switch installed at any one of the conveyance unit and the guide member, wherein a detection protrusion is installed at the other of the conveyance unit and the guide member, and when the detection protrusion enters the limit switch, a lowering operation of the support unit is stopped.

8. The vertical motion adjuster according to claim 7, further comprising a driving member configured to rotate the rotary member.

9. The vertical motion adjuster according to claim 1, wherein the conveyance unit and the support unit are hinged through a hinge unit.

10. The vertical motion adjuster according to claim 9, wherein the hinge unit comprises:

protrusion members installed at both sides of the conveyance unit;

connecting members installed at both sides of the support unit; and hinge members passing through the protrusion members and the connecting members.

11. The vertical motion adjuster according to claim 1, wherein the moxibustion device is mounted on a support frame installed at the support side of the support unit, and the support frame is pivotally installed at a pivot shaft.

12. The vertical motion adjuster according to claim 11, further comprising a first resilient member having a first end supported by the support unit and a second end supported by the support frame, wherein the first resilient member is installed at the pivot shaft, and wherein the first resilient member is configured to apply a resilient force to the support frame such that one moxibustion device adjacent to a coupling position of the conveyance unit and the support unit is moved upward.

13. The vertical motion adjuster according to claim 12, further comprising a temperature detecting member configured to detect a temperature of the moxibustion device, and a second resilient member installed at the temperature detecting member, the second resilient member configured to apply a resilient force in a direction in which the moxibustion device is moved upward.

14. The vertical motion adjuster according to claim 11, wherein the moxibustion device is a first moxibustion device, the vertical motion adjuster further comprising a second moxibustion device, wherein an upwardly moving distance of the first moxibustion device adjacent to a coupling position of the conveyance unit and the support unit is different from an upwardly moving distance of the second moxibustion device opposite to the first moxibustion device with respect to the pivot shaft.

15. The vertical motion adjuster according to claim 14, wherein the upwardly moving distance of the first moxibustion device is larger than the upwardly moving distance of the second moxibustion device.

16. The vertical motion adjuster according to claim 15, wherein a protrusion extends downward from a lower end of the support frame, inclination angles are formed at a lower end of the protrusion, and the inclination angle directed toward the first moxibustion device is set to be smaller than the inclination angle directed toward the second moxibustion device.

17. The vertical motion adjuster according to claim 15, further comprising an absorption member protruding upward toward the lower end of the support frame, wherein the absorption member is formed at the support side of the support unit, and a height of the absorption member protruding upward toward the first moxibustion device is larger than that of the absorption member protruding upward toward the second moxibustion device.

18. The vertical motion adjuster according to claim 1, wherein a coupling position of the conveyance unit and the support unit is disposed at a position lower than an upper end surface of the support unit.

19. The vertical motion adjuster according to claim 18, wherein the conveyance unit and the support unit are hinged by a hinge unit, wherein the hinge unit comprises:

protrusion members installed at both sides of the conveyance unit;

connecting members installed at both sides of the support unit; and hinge members passing through the protrusion member and the connecting member, one end of the connecting member extending downward to be inserted into the conveyance unit.

20. The vertical motion adjuster according to claim 19, wherein at least one of the hinge members includes a pin hole through which a pin passes.

21. The vertical motion adjuster according to claim 18, wherein the conveyance unit includes an accommodating space into which the support unit enters.

22. The vertical motion adjuster according to claim 1, wherein the opening is formed in a center of the conveyance unit.

23. The vertical motion adjuster according to claim 22, wherein a reinforcement rib formed along an edge of the conveyance unit to surround the opening is formed at a base surface of the conveyance unit, and wherein the reinforcement rib is one of a plurality of reinforcement ribs formed in a lengthwise direction of the conveyance unit.

24. The vertical motion adjuster according to claim 1, further comprising a cable configured to connect a circuit member installed under the conveyance unit and a circuit member installed under the support unit, a long hole through which the cable passes is formed in the conveyance unit, and the long hole has a length in a lengthwise direction larger than a length in a widthwise direction.

25. The vertical motion adjuster according to claim 24, further comprising a projection surface curved toward a center of the long hole, the projection surface formed at an inner surface in the lengthwise direction of the long hole.

26. The vertical motion adjuster according to claim 24, further comprising a cover member installed at an inner surface in the lengthwise direction of the long hole.

* * * * *